United States Patent
Meyers

(10) Patent No.: US 9,770,566 B2
(45) Date of Patent: Sep. 26, 2017

(54) SPIROMETER DEVICE WITH VISUAL AID FOR THERAPEUTIC BREATHING

(71) Applicant: Jessica Meyers, Dearborn, MI (US)

(72) Inventor: Jessica Meyers, Dearborn, MI (US)

( * ) Notice: Subject to any disclaimer, the term of this patent is extended or adjusted under 35 U.S.C. 154(b) by 504 days.

(21) Appl. No.: 14/178,923

(22) Filed: Feb. 12, 2014

(65) Prior Publication Data

US 2014/0224251 A1    Aug. 14, 2014

Related U.S. Application Data

(60) Provisional application No. 61/764,397, filed on Feb. 13, 2013.

(51) Int. Cl.
| | |
|---|---|
| *A61M 16/00* | (2006.01) |
| *A61B 5/093* | (2006.01) |
| *A63B 23/18* | (2006.01) |
| *A61B 5/091* | (2006.01) |
| *A61B 5/00* | (2006.01) |
| *A63B 71/06* | (2006.01) |

(52) U.S. Cl.
CPC ......... *A61M 16/0051* (2013.01); *A61B 5/091* (2013.01); *A61B 5/093* (2013.01); *A61B 5/744* (2013.01); *A63B 23/18* (2013.01); *A63B 2071/0602* (2013.01); *A63B 2071/0647* (2013.01); *A63B 2225/62* (2013.01)

(58) Field of Classification Search
CPC .......... A61M 16/0051; A61M 16/0057; A61M 16/0075; A61M 16/08; A61B 5/091; A61B 5/093; A61B 5/0935; A61B 5/095; A61B 5/7425; A61B 5/744; A63B 23/18
See application file for complete search history.

(56) References Cited

U.S. PATENT DOCUMENTS

| | | | | |
|---|---|---|---|---|
| 642,149 | A * | 1/1900 | McKenzie | A61B 5/093 116/272 |
| 3,420,225 | A * | 1/1969 | Smith, Jr. | A61B 5/091 417/473 |
| 3,695,608 | A | 10/1972 | Hanson | |
| 3,848,583 | A * | 11/1974 | Parr | A61B 5/093 600/541 |
| 3,936,048 | A | 2/1976 | Dunlap et al. | |
| 4,025,070 | A | 5/1977 | McGill et al. | |
| RE29,317 | E * | 7/1977 | Mosley | G09B 23/28 434/272 |
| 4,138,105 | A * | 2/1979 | Hunger | A63B 23/18 482/13 |
| 4,143,872 | A | 3/1979 | Havstad et al. | |
| 4,221,381 | A * | 9/1980 | Ericson | A63B 23/18 482/13 |
| 4,241,740 | A | 12/1980 | Brown | |

(Continued)

FOREIGN PATENT DOCUMENTS

EP        0027154 A1 *  4/1981  ............. A61B 5/093

*Primary Examiner* — Kathryn E Ditmer
(74) *Attorney, Agent, or Firm* — Kagan Binder, PLLC

(57) ABSTRACT

A spirometer-type device is described that is designed to improve patient compliance with therapeutic breathing for improved pulmonary function. In an example embodiment, a display of human lungs is provided that visually elevate with inhalation. A patient's progress is visualized with a featured conspicuous level marker and upward motions of lungs that are seen from both sides of the device.

17 Claims, 3 Drawing Sheets

(56) References Cited

U.S. PATENT DOCUMENTS

| | | | |
|---|---|---|---|
| 4,299,236 A * | 11/1981 | Poirier | A61B 5/093 482/13 |
| 4,323,078 A | 4/1982 | Heimlich | |
| 4,324,260 A * | 4/1982 | Puderbaugh | A61B 5/093 482/13 |
| 4,363,328 A | 12/1982 | Poirier et al. | |
| 4,391,283 A * | 7/1983 | Sharpless | A61B 5/0875 482/13 |
| 4,441,506 A | 4/1984 | McCombs et al. | |
| 4,444,202 A | 4/1984 | Rubin et al. | |
| 4,635,647 A | 1/1987 | Choksi | |
| 4,973,047 A | 11/1990 | Norell | |
| 5,658,221 A | 8/1997 | Hougen | |
| 5,899,832 A | 5/1999 | Hougen | |
| 6,656,129 B2 * | 12/2003 | Niles | A61B 5/0875 600/532 |
| 7,334,581 B2 | 2/2008 | Doshi | |
| 2009/0239711 A1 * | 9/2009 | Foley | A63B 21/0085 482/13 |

* cited by examiner

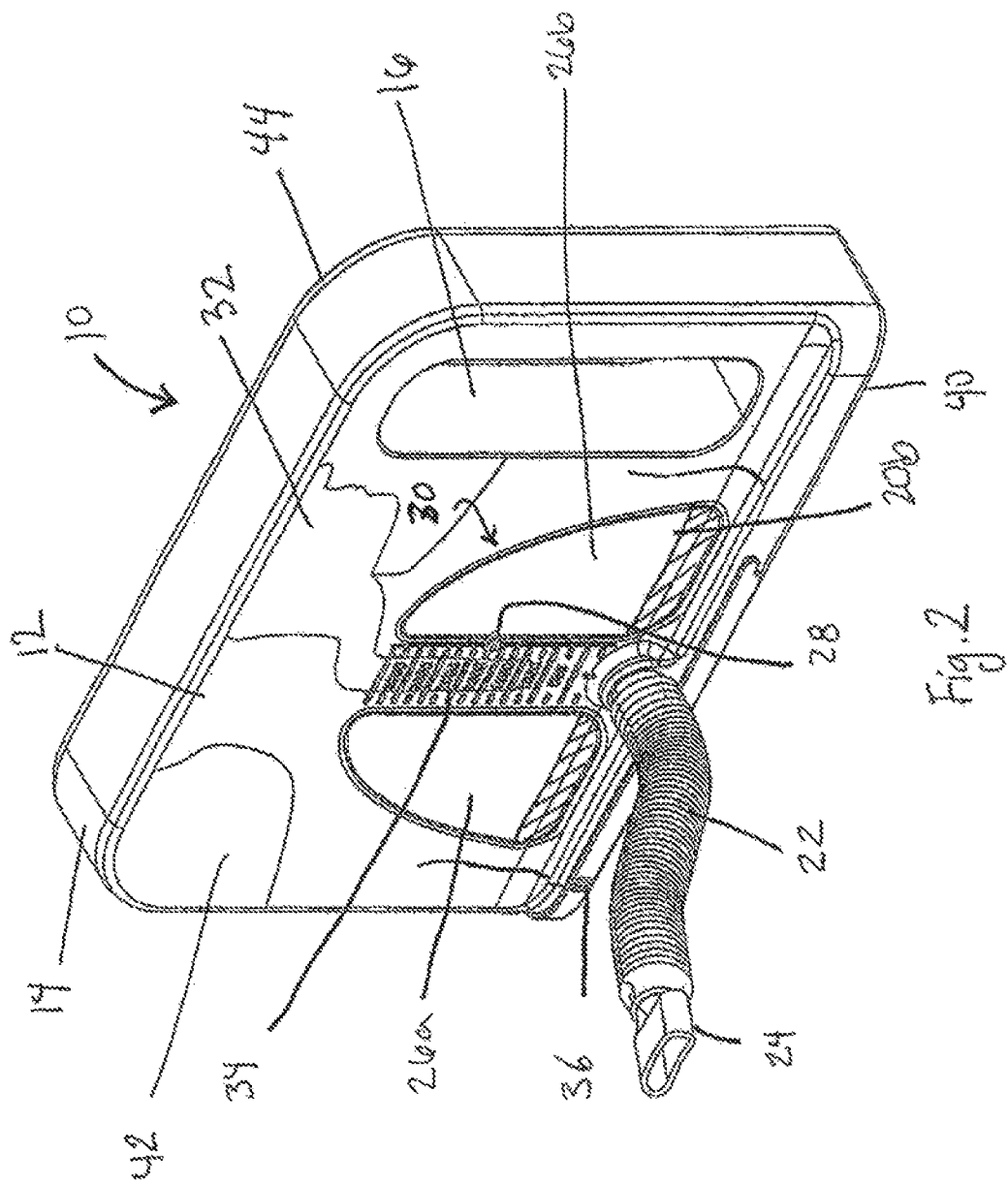

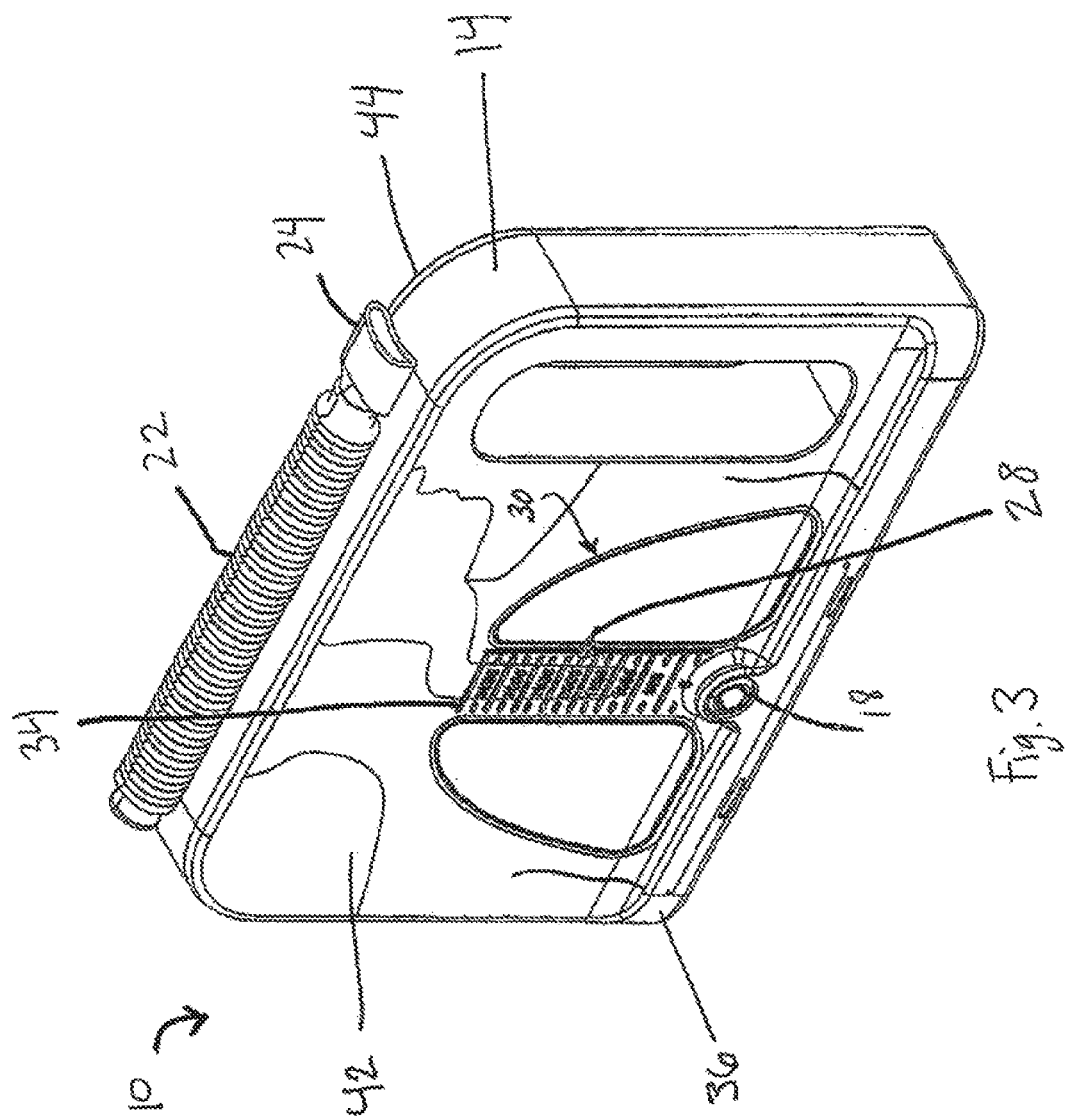

SPIROMETER DEVICE WITH VISUAL AID FOR THERAPEUTIC BREATHING

CLAIM OF PRIORITY

This application claims the benefit of and priority to U.S. Provisional Patent Application No. 61/764,397, filed Feb. 13, 2013 and titled "SPIROMETER DEVICE WITH VISUAL AID FOR THERAPEUTIC BREATHING" which application is incorporated herein by reference in its entirety.

FIELD OF THE INVENTION

The invention relates generally to a spirometer with a visual aid that assists in therapeutic breathing.

BACKGROUND OF THE INVENTION

Spirometers are generally devices used by physicians and medical professionals to gauge lung and breathing performance of patients that may have asthma, COPD or other breathing ailments, and patients recovering from surgery. When readings on the spirometers change, the therapy or medication may change. A change in spirometer readings may even prompt the patient to call a doctor or nurse for advice. Unfortunately, at times early detection of deteriorating breathing problems is not possible, which could avoid trips to the emergency room.

Another challenge in using spirometers that are currently on the market is that their complexity requires explanation to the patients about how they should be used. These devices are not intuitive in their operation and how they can help patients. Currently there are a number of solutions for assisting with therapeutic breathing. Some of these solutions attempt to provide a visual measurement, but these solutions fail to meet the needs of the industry because they do not make it clear what is being measured nor how the device is helping the user improve their lung health.

Therefore, there currently exists a need in the industry for an apparatus and method for measuring pulmonary health improvement for a patient and providing feedback to the patient on how effectively he is using such an apparatus.

SUMMARY OF THE INVENTION

The various embodiments described herein advantageously fills the aforementioned deficiencies by providing a spirometer device that assists in therapeutic breathing and provides better instruction (and visualization) and performance indicators to the user or patient. The various advantages include but are not limited to: assisting a patient to improve pulmonary function through inhalation by giving a patient a visual demonstration of how the device is working and how the patient is improving with continued use; early and clear indication to a patient of slow loss of pulmonary function or breathing capacity (thereby allowing early detection of therapy, treatment or drug malfunction or ineffectiveness); and a lightweight and portable device to improve patient compliance.

In one example embodiment, a breathing tube is connected to a box or housing that has an image of lungs on it. When the user inhales into the tube, the volume of air moves a measurement marker, which is a mark on a bellow that aligns to a column marking when a user inhales, (along a visual aid such as a displayed set of lungs), to show how well they are breathing or how much lung capacity they have. When the user inhales, the bellow moves which is illustrated by the visual aide that shows expanding lungs and the lungs filling with air. In a related embodiment, the spirometer device is configured to operate in the opposite direction by having the user exhale into device to fill the inflatable bellow.

In a related embodiment, a patient experiences an increase in difficulty in inhaling into the device tube when a first level adjuster (in this example, a leveler member located on the base of the spirometer unit) is pulled outward to regulate pressure in the device. This exposes one or more holes at the bottom or base of the unit to increase the difficulty of raising the visual lung members or bellows (a form of exercising the breathing and lung capacity of the patient as the patient's health is improving), which increases or decreases a breathing pressure to a user.

In yet another related embodiment, the housing of the spirometer unit provides a simplistic image of lungs within a human on both sides of the unit that moves upward with inhalation that can be seen by both a patient, on one side, and a medical professional or aide on the other side. The display of the lungs helps a patient understand what the device is used for which is a distinct difference from other spirometers on the market.

One example embodiment of the invention includes providing a respiratory therapy device comprised of a housing, an inflatable bellow member, and a breathing tube. In this example embodiment, the housing includes a base, front wall, and a rear wall. The front wall has at least one opening and includes an image of an upper half of a human torso. The inflatable bellow member is located within the housing and is viewable through the opening. The breathing tube is coupled to an airway port on the front wall of the housing and is in fluid communication with the bellow member. The viewable portion of the bellow member is capable of simulating a human lung, which provides visual feedback to a user when performing a respiratory exercise.

In another embodiment of the invention, a method of measuring a respiratory condition of a patient is provided. The method includes providing a respiratory device as described above and having the patient breathe through the breathing tube while viewing the movement of the inflatable bellow. The patient maintains a lung condition for a predetermined time and records a height of the inflatable bellow on a measurement scale located on the front wall of the device.

In yet another embodiment of the invention, a respiratory therapy device kit is provided. The kit includes a respiratory therapy device comprising a housing, an inflatable bellow member, and a breathing tube. The housing includes a base, front wall, and a rear wall. The front wall includes an image of a human profile wherein two transparent openings resemble a pair of human lungs. The inflatable bellow member is located within the housing and is viewable through the opening. The breathing tube is attachable to the front wall of the housing at an airway port and is in fluid communication with the bellow member. The viewable portion of the bellow member is capable of simulating a human lung, which provides visual feedback to a user when performing a respiratory exercise.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

BRIEF DESCRIPTION OF THE DRAWINGS

FIG. 2 illustrates an isometric view of the spirometer; and

FIG. 3 illustrates the front of the spirometer when not in use, ready for portability or storage.

DETAILED DESCRIPTION OF THE INVENTION

Figure 1:
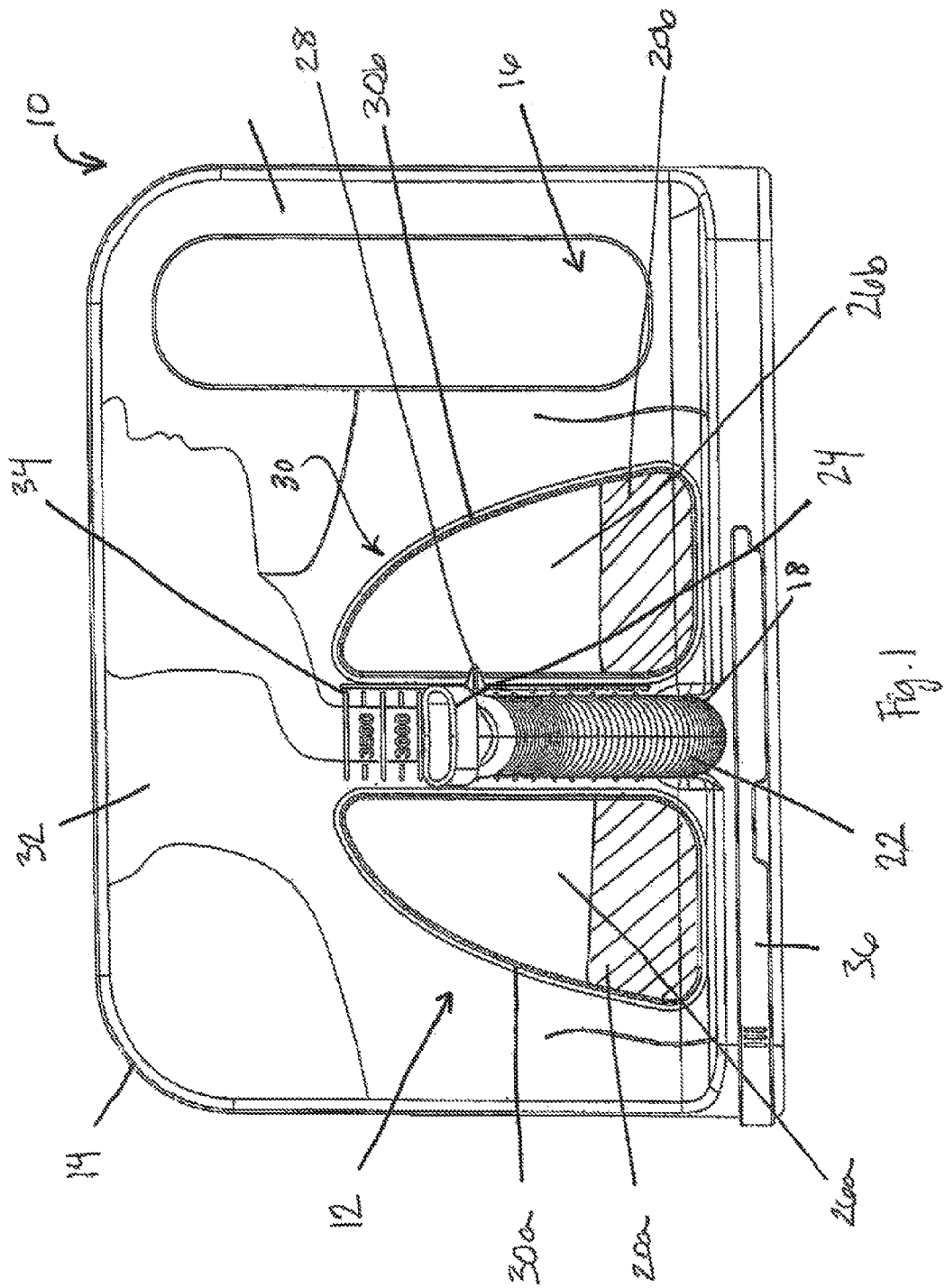
FIG. 1 illustrates a front view of a spirometer device according to the teachings herein ready for use.

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

The various embodiments described herein are directed to a spirometer device and method of use that simplifies use thereof and promotes patient compliance due to its simplicity of operation, immediate visual feedback and its lightweight and portable design.

Referring now to the figures, FIGS. 1 and 2 illustrate one example embodiment of a spirometer device 10 that includes a housing 14 having a base 40, front wall 42, and back wall 44. Front wall 42 comprises a display assembly 12, a handle 16, and airway port 18 in communication with at least one bellow 20a. A breathing tube 22 connects to airway port 18 at one end and comprises a mouthpiece 24 at an opposite end. Airway port 18 may include a filter so as to keep particulate matter out of bellow 20.

The display assembly or image 12 includes a human lung display 30, comprised of lungs 30a and 30b, and human head 32 to depict an example image of a user. In an embodiment, display assembly 12 includes windows 26 with at least one window 26a on the front wall 42 to show the inside of the housing 14 (and complementary window 26b on the opposite side). The back wall 44 may also include at least one window similar to 26a. In a related embodiment, windows 26a, 26b may provide a view of the first and second bellow members 20a, 20b.

When in use, as a user inhales from breathing tube 22, the bellow 20 rises, which can be seen through window 26. When a user exhales into breathing tube 22, bellow 20 lowers, which can be seen through window 26. Window 26 may be made from any transparent or translucent materials such as glass or plastic. A moveable measurement marker 28 may be moved up and down on a measurement column 34 located next to window 26. During use, measurement marker 28 can be used to track progress and gauge pulmonary function.

In a related embodiment, front wall 42 includes a physical counter to keep track of the number of uses by the patient in one day or one week. In another embodiment, spirometer device 10 can include Wi-Fi or wireless capability to connect with a smartphone application to track the user's therapy.

Housing 14 may also include an airway adjusting member 36 which may increase or decrease the difficulty of breathing in device 10. In a closed position, adjusting member 36 may cover one or more holes (not shown) in housing 14, and in an open position, adjusting member 36 may allow one or more holes (not shown) to be open.

In one example embodiment, when the user inhales from breathing tube 22, the volume of air the user inhaled expands and thereby increases the height of bellow 20. In another embodiment, measurement marker 28 may automatically move along measurement column 34 with the rise of bellow 20. Measurement column 34 may also be manually marked to show how well the user is breathing or the lung capacity of the user. In a related embodiment, device 10 is configured to operate in the opposite direction by having the user exhale to change the respiratory exercise of the user to demonstrate bellow member 20 expansion as the user blows air into the device, which may be seen through windows 26 on display assembly 12.

In a related embodiment, a user may experiences an increase in difficulty when inhaling or exhaling through breathing tube 22 when adjusting member 36 is opened. This exposes one or more holes (not shown) the bottom or base of housing 14 to increase the difficulty of raising bellows 20 (a form of exercising the breathing and lung capacity of the user as the user's health is improving). Since the user experiences an increase in difficulty when adjusting member 36 is pulled outward, exposing one or more holes (not shown), adjusting member 36 may also be closed to decrease the difficulty of breathing.

Referring now to FIG. 3, in yet another related embodiment, front wall 42 of housing 14 of device 10 provides a simplistic image of lung display 30 within a human torso on either or both sides of device 10. Bellows 20, which are located within housing 14 and can be seen through window 26. Bellows 20 move upward with inhalation. In another embodiment, display assembly 12 is located on both front wall 42 and back wall 44 of housing 14, which allows both a user and a medical professional or aide to see the movement on opposite sides of device 10. This two-sided display assembly 12 allows both the user and medical professional or aide to see the rise and fall of bellows 20 and progress of the user.

For portability, breathing tube 22 may be removed from airway port 18 for easy travel and storage. In an example, breathing tube 22 may be stored on the top of housing 14. Breathing tube 22 may be made from a variety of materials that are flexible and/or collapsible, such as plastics, or other materials known in the art. A cover (not shown) may be placed over airway port 18 when breathing tube 22 is not connected to keep bellows 20 free of debris.

In one example embodiment of a method of improving lung function with device 10, a user (or patient) sits on the edge of a chair or bed if possible, or sits up as far as they can in bed. The user holds device 10 in an upright position (wherein display assembly 12 is oriented in an upright position, base 40 is facing the ground) and places mouthpiece 24 of breathing tube 22 in their mouth and seals their lips tightly around it. Next, the user inhales as slowly and as deeply as possible, raising bellows 20 toward the top of lung display 30. Measurement marker 28 is in measurement column 34 at a bellow level reached or a desired goal level. The user then holds their breath as long as possible (or for at least five seconds) and allows bellow 20 to deflate and fall to the bottom of housing 14. Next, the user rests for a few seconds and repeats the previous steps, for example, at least 10 times every hour when the user is awake. The position of measurement marker 28 on measurement column 34 can show the previous level of bellows 20 to represent a goal.

Measurement marker 28 may be used as a goal to work toward during each repetition. After each set of 10 deep breaths, the user may practice coughing to be sure their lungs are clear.

The following patents are incorporated by reference in their entireties: U.S. Pat. Nos. 6,656,129; 4,324,260; and 4,363,328.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

The invention claimed is:

1. A respiratory therapy device comprising:
    a housing having a base, a front wall and a rear wall, a portion of the front wall having at least one window; said front wall including an image thereon of human lungs disposed about said at least one window;
    a first and a second inflatable bellow member disposed side by side within said housing, portions of which are viewable through said at least one window; and
    a breathing tube adapted to be coupled to an airway port disposed on said front wall of said housing, said airway port in fluid communication with said bellow members;
    wherein the viewable portions of said bellow members through said window with the image of the human lungs disposed thereabout simulate human lungs as the bellow members rise and fall to provide visual feedback to a user when performing a respiratory exercise.

2. The respiratory device of claim 1 wherein said housing comprises an airway adjusting member to regulate pressure in the device by externally moving the airway adjusting member to expose a hole in the housing.

3. The respiratory device of claim 2 wherein movement of said airway adjusting member increases or decreases a breathing pressure to a user as one or more holes are opened or exposed.

4. The respiratory device of claim 1 wherein said housing further comprises a measurement column scale with a slide marker member, said slide marker member providing the user with a visual feedback of the user's respiratory condition.

5. The respiratory exercise device of claim 1 wherein the at least one window includes one of a transparent or translucent cover.

6. The respiratory exercise device of claim 1 wherein said housing includes two windows on said front wall.

7. The respiratory exercise device of claim 1 wherein the rear wall includes a second window exposing said bellow members and movement thereof from the rear wall of the respiratory device.

8. The respiratory exercise device of claim 1 wherein said bellow members are configured to change the respiratory exercise of the user to demonstrate bellow member expansion as the user blows or exhales through the breathing tube air into the device.

9. A respiratory therapy device kit comprising:
    a housing having a base, a front wall and a rear wall, a portion of the front wall having two transparent windows, said front wall including an image thereon of a human profile disposed about said windows resembling or depicting a set of human lungs;
    a first and a second inflatable bellow member disposed side by side within said housing, portions of which are viewable through said windows; and
    an attachable breathing tube adapted to be coupled to an airway port disposed on said front wall of said housing, said airway port in fluid communication with said bellow members;
    wherein the viewable portions of said bellow members through said windows with the image of the human profile disposed thereabout simulate human lungs as the bellow members rise and fall to provide visual feedback to a user when performing a respiratory exercise, and wherein the housing further comprises an airway adjusting member to regulate pressure in the respiratory therapy device when externally moved to expose a hole in the housing to decrease or increase difficulty in breathing.

10. A method of measuring a respiratory condition of a patient comprising the steps of:
    a) providing a respiratory therapy device that includes
        a housing with a base, a rear wall and a front wall, a portion of the front wall having at least one window, said front wall including an image thereon of human lungs disposed about said at least one window;
        a first and a second inflatable bellow member disposed side by side within said housing, portions of which are viewable through said at least one window; and
        a breathing tube adapted to be coupled to an airway port disposed on said front wall of said housing, said airway port in fluid communication with said bellow members;
    b) breathing through said breathing tube while the patient views a corresponding movement of said inflatable bellow members which simulate human lungs as the bellow members rise and fall to provide visual feed back to the patient when performing a respiratory exercise;
    c) maintaining a lung condition for a predetermined time; and
    d) recording a height of said inflatable bellows on a measurement scale disposed on said front wall.

11. The method of claim 10 further comprising the step of resting for a period of time and repeating steps b) through d).

12. The method of claim 10 wherein the step of breathing includes exhaling into the device.

13. The method of claim 12 wherein the step of maintaining the lung condition includes not inhaling for a brief period of time.

14. The method of claim 10 wherein the step of breathing includes inhaling into the device.

15. The method of claim 14 wherein the step of maintaining the lung condition includes not exhaling for a brief period of time.

16. The method of claim 10 further comprising the step of adjusting an airway level member on the respiratory device, thereby increasing or decreasing an airway pressure in the device.

17. The method of claim 11 wherein the step of recording the height includes moving a slide marker on the measurement scale after each set of respiratory exercises to provide feedback on the respiratory condition of the patient.

* * * * *